US009248239B2

(12) United States Patent
Leak et al.

(10) Patent No.: US 9,248,239 B2
(45) Date of Patent: Feb. 2, 2016

(54) DRUG DELIVERY DEVICE HAVING LINKED DOSE DIAL COMPONENTS

(75) Inventors: David Martin Leak, Lake Hopatcong, NJ (US); David Aubrey Plumptre, Worcestershire (GB); Malcolm Stanley Boyd, Warwickshire (GB); Daniel Thomas De Sausmarez Lintell, Warwickshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 13/885,324

(22) PCT Filed: Nov. 28, 2011

(86) PCT No.: PCT/EP2011/071111
§ 371 (c)(1),
(2), (4) Date: May 14, 2013

(87) PCT Pub. No.: WO2012/072535
PCT Pub. Date: Jun. 7, 2012

(65) Prior Publication Data
US 2013/0237924 A1 Sep. 12, 2013

Related U.S. Application Data (60) Provisional application No. 61/432,710, filed on Jan. 14, 2011.

(30) Foreign Application Priority Data

Nov. 29, 2010 (EP) .................................. 10192842

(51) Int. Cl.
*A61M 5/315* (2006.01)
*A61M 5/19* (2006.01)
*A61M 5/31* (2006.01)

(52) U.S. Cl.
CPC .............. *A61M 5/3155* (2013.01); *A61M 5/19* (2013.01); *A61M 5/31596* (2013.01); *A61M 2005/3142* (2013.01)

(58) Field of Classification Search
CPC . A61M 5/19; A61M 5/31596; A61M 5/3155; A61M 2005/3142
USPC ......... 604/71, 82–92, 191, 207–211, 218–31, 604/246; 222/145.1, 145.7, 309, 390
See application file for complete search history.

(56) References Cited

U.S. PATENT DOCUMENTS 5,253,785 A * 10/1993 Habe ....................... A61M 5/19
222/135
5,582,598 A * 12/1996 Chanoch ....................... 604/208

(Continued)

FOREIGN PATENT DOCUMENTS

DE 102007026083 11/2008
WO 94/22507 10/1994
WO 2010/077280 7/2010

OTHER PUBLICATIONS

International Search Report and Written Opinion for Int. App. No. PCT/EP2011/071111, completed Jan. 4, 2012.

(Continued)

*Primary Examiner* — Theodore Stigell
*Assistant Examiner* — Amber Stiles
(74) *Attorney, Agent, or Firm* — McDonnell Boehnen Hulbert & Berghoff LLP (57) ABSTRACT

A drug delivery device for co-delivery of two medicaments. The drug delivery device has a dose setter, a first dose dial component, a second dose dial component, and a collar. The first dose dial component is configured to select a first dose of a first medicament, and the first dose dial component is operably connected to the dose setter. The second dose dial component is configured to select a second dose of a second medicament. In addition, the first dose dial component and the second dose dial component are connected to the collar. The collar is configured to be moved in a proximal direction by actuation of the dose setter. Further, when the collar is moved in a proximal direction, the first dose dial component and the second dose dial component are configured to move proximally to set a dose "A" for the first medicament with the first dose dial component and set a dose "B" for the second medicament with the second dose dial component.

14 Claims, 6 Drawing Sheets

(56) References Cited

U.S. PATENT DOCUMENTS

| | | | |
|---|---|---|---|
| 5,584,815 A * | 12/1996 | Pawelka et al. | 604/191 |
| 2005/0143653 A1 * | 6/2005 | Fukuda | 600/432 |
| 2010/0168677 A1 | 7/2010 | Gabriel et al. | |
| 2011/0270222 A1 * | 11/2011 | Wei et al. | 604/506 |

OTHER PUBLICATIONS

International Preliminary Report on Patentability for Int. App. No. PCT/EP2011/071111, mailed Jun. 13, 2013.

* cited by examiner

DRUG DELIVERY DEVICE HAVING LINKED DOSE DIAL COMPONENTS

CROSS REFERENCE TO RELATED APPLICATIONS

The present application is a U.S. National Phase Application pursuant to 35 U.S.C. §371 of International Application No. PCT/EP2011/071111 filed Nov. 28, 2011, which claims priority to European Patent Application No. 10192842.2 filed Nov. 29, 2010, and U.S. Provisional Patent Application No. 61/432,710, filed Jan. 14, 2011. The entire disclosure contents of these applications are herewith incorporated by reference into the present application.

FIELD OF THE DISCLOSURE

This present patent application relates to medical devices and methods of delivering at least two drug agents from separate reservoirs using devices having linked dose dial components and a single dispense interface. A single delivery procedure initiated by the user causes a non-user settable dose of a second drug agent and a user-variable set dose of a first drug agent to be delivered to the patient. The drug agents are contained in two or more multiple dose reservoirs, containers or packages, each containing independent (single drug compound) or pre-mixed (co-formulated multiple drug compounds) drug agents. The disclosed method and system is of particular benefit where the therapeutic response can be optimized for a specific target patient group, through control and definition of the therapeutic profile.

BACKGROUND

Certain disease states require treatment using one or more different medicaments. Some drug compounds need to be delivered in a specific relationship with each other in order to deliver the optimum therapeutic dose. The disclosed method and system is of particular benefit where combination therapy is desirable, but not possible in a single formulation for reasons such as, but not limited to, stability, compromised therapeutic performance and toxicology.

For example, in some cases it might be beneficial to treat a diabetic with a long-acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two active medicaments or "agents" simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example, one or more actives may require a titration period to gradually introduce a patient to a "maintenance" dose. A further example would be if one active requires a non-user settable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems arise where a multi-drug compound therapy is required, because many users cannot cope with having to use more than one drug delivery system or make the necessary accurate calculation of the required dose combination, especially where the relationship between the two or more medicaments is non-linear. This is especially true for users with dexterity or computational difficulties.

Accordingly, there exists a strong need to provide devices and methods for the delivery of two or more medicaments in a single injection or delivery step that is simple for the user to perform. The disclosed method and system overcomes the above-mentioned problems by providing separate storage containers for two or more active drug agents that are then only combined and/or delivered to the patient during a single delivery procedure. Setting a dose of one medicament automatically fixes or determines the dose of the second medicament (i.e. non-user settable). The disclosed method and system also gives the opportunity for varying the quantity of one or both medicaments. For example, one fluid quantity can be varied by changing the properties of the injection device (e.g. dialing a user variable dose or changing the device's "fixed" dose). As such, the disclosed system and method may achieve a wide variety of target therapeutic profiles.

These and other advantages will become evident from the following more detailed description of the invention.

SUMMARY

The disclosed system and method allows complex combination of multiple drug compounds within a single device. In particular, the disclosed system and method allows the user to set and dispense a multi-drug compound device through one single dose setter and a single dispense interface. This single dose setter controls the dose setting mechanism of the device such that a predefined combination of the individual drug compounds is delivered when a single dose of one of the medicaments is set and dispensed through the single dispense interface. Although principally described in this application as an injection device, the basic principle could be applicable to other forms of drug delivery, such as, but not limited to, inhalation, nasal, ophthalmic, oral, topical, and like devices.

By defining the therapeutic relationship between the individual drug compounds, Applicants' delivery device would help ensure that a patient/user receives the optimum therapeutic combination dose from a multi-drug compound device without the inherent risks associated with multiple inputs, where the user has to calculate and set the correct dose combination every time they use the device. The medicaments can be fluids, defined herein as liquids, gases or powders that are capable of flowing and that change shape at a steady rate when acted upon by a force tending to change its shape. Alternatively, one of the medicaments may be a solid that is carried, solubilized or otherwise dispensed with another fluid medicament.

This disclosed system is of particular benefit to users with dexterity or computational difficulties as the single input and associated predefined therapeutic profile removes the need for them to calculate their prescribed dose every time they use the device and the single input allows considerably easier setting and dispensing of the combined compounds.

In an embodiment of the proposed system, a master drug compound, such as insulin, is contained within a primary reservoir and a secondary medicament is contained within a secondary reservoir. When a dose of the primary compound is set and dispensed, the secondary compound is activated/delivered on dispense of the primary compound. Although Applicants' present patent application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with Applicants' proposed system and method.

For the purposes of Applicants' system and method the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg (B32) human insulin; Lys(B3), Glu(B29) human insulin; Lys (B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

One embodiment of Applicants' disclosure relates to a drug delivery system to deliver two or more medicaments through a single dose setter and a single dispense interface, where the device has a housing containing a single user-operable dose setter operably connected to a primary reservoir of a first medicament containing multiple doses of at least one drug agent. A dose button is operably connected to the primary reservoir of medicament and a single dispense interface is configured for fluid communication with the primary reservoir. A secondary reservoir of a second medicament containing multiple doses of at least one drug agent is configured for fluid communication to the single dispense interface. A single activation of the dose setter by a user sets a dose from the primary reservoir and automatically sets a non-user settable dose of the second medicament. A single activation of the dose button causes the set dose of the first medicament from the primary reservoir and the non-user settable dose of the second medicament to be expelled through the single dispense interface.

This dose button can be any type of mechanism that triggers the delivery procedure, whether driven mechanically or through a combination of electronics and mechanics. The button can move or be a touch sensitive virtual button, for example, a touch sensitive screen. Applicants' system has a single dispense interface configured for fluid communication with the primary reservoir and with a secondary reservoir of medicament containing at least one drug agent. The drug dispense interface can be any type of outlet that allows the two or more medicaments to exit the system and be delivered to the patient. Types of interfaces include hollow needles, catheters, atomizers, pneumatic injectors, or needle-less injectors, mouthpieces, nasal-applicators and the like interfaces.

The secondary reservoir contains multiple doses of medicament. The system is designed such that a single activation of the dose button causes the user set dose of medicament from the primary reservoir and a non-user set dose of medicament from the second reservoir to be expelled through the single dispense interface. By user settable dose it is meant that the user (patient or health care provider) can physically manipulate the device to set a desired dose. Additionally, the user settable dose can be set remotely through the use of wireless communication (Bluetooth, WiFi, satellite, etc.) or the dose could be set by another integrated device, such as a blood glucose monitor after performing a therapeutic treatment algorithm. By non-user set dose it is meant that the user (or any other input) cannot independently set or select a dose of medicament from the secondary reservoir. In other words, when the user (or another input as described above) sets the dose of the primary medicament in the primary reservoir, the dose of the second medicament is automatically set.

In an example of Applicants' proposed system, a drug delivery device includes two dose dial components linked to one another by a collar. In this example, the drug delivery device has a dose setter, a first dose dial component, a second dose dial component, and a collar. The first dose dial component is configured to select a first dose of a first medicament, and the first dose dial component is operably connected to the dose setter. The second dose dial component is configured to select a second dose of a second medicament. In addition, the first dose dial component and the second dose dial component are each connected to the collar. This collar is configured to be moved in a proximal direction by actuation of the dose setter. Further, when the collar is moved in a proximal direction, the first dose dial component and the second dose dial component are configured to move proximally to set a dose "A" for the first medicament with the first dose dial component and set a dose "B" for the second medicament with the second dose dial component.

In an example, of this drug delivery device the first dose dial component comprises a first threaded arrangement configured to rotate the first dose dial component, and the second dose dial component comprises a second threaded arrangement configured to rotate the second dose dial component. Depending on the desired dose profile, the second threaded arrangement may be the same as or different than the first threaded arrangement. The first threaded arrangement may comprise a helical thread of a constant pitch, wherein the second threaded arrangement may comprise a first portion and a second portion. The first portion may be a helical thread and the second portion may be a straight thread. In another example the first threaded arrangement may comprise a helical thread of a constant pitch, and the second threaded arrangement may comprise a helical thread of a different constant pitch. Furthermore the first threaded arrangement may comprise a helical thread of a constant pitch, and the second threaded arrangement may comprise a helical thread of a variable pitch.

In yet another embodiment the drug delivery device of the present disclosure comprises a priming arrangement, configured to allow dispense of only one medicament. This could be beneficial to prime the device with, for example, a small dose of one medicament. The priming arrangement may be a button. The drug delivery device further comprises a collar configured to operably connect to the first dose dial component and to the second dose dial component. The button may be arranged at the collar. The priming arrangement may be configured to disengage the second dose dial component from the first dose dial component. In one example the priming arrangement may be configured to disengage the second dose dial component from the collar preventing the second dose dial component to move proximally when the collar is moved in a proximal direction. After dispensing the priming dose the second dose dial component and the collar may reengage.

Applicants' present disclosure also is generally directed to a method of dispensing a fixed dose of one medicament and a variable dose of another medicament from separate reservoirs that involves the steps of first setting a dose of a first medicament contained in a primary reservoir of a drug delivery device having a single dose setter. This setting of the first dose automatically sets the dose from a secondary reservoir without a separate input by the user. A dose button is activated that moves both the set dose of the first medicament from the primary reservoir and the automatically set non-user settable dose from the secondary reservoir through a single dispense interface. In an example, the method comprises forcing a first dose dial component to rotate a different amount than a second dose dial component.

The combination of compounds as discrete units or as a mixed unit can be delivered to the body via an integral needle. This would provide a combination drug injection system that, from a user's perspective, would be achieved in a manner that very closely matches the currently available injection devices that use standard needles. One possible delivery procedure would involve the following steps:

1. Attach a single dispense interface, such as a needle hub, to the distal end of the injection device such that the proximal end of the single dispense interface is in fluidic communication with both the primary compound and secondary compound.

2. Dial up (i.e., set) the injection device such that it is ready to dispense the desired dose of the primary compound. As the single dose setter sets the dose of the primary compound, a predefined non-user settable dose of the secondary compound is automatically set at the same time.

3. Insert or apply the distal end of the single dispense interface to the patient at or into the desired administration site. Dose the primary compound by activating a single dose button, which also causes the secondary compound to automatically dispense.

The drug delivery system of Applicants' disclosure may be designed in such a way as to limit its use to exclusive primary and secondary reservoirs through employment of dedicated or coded features. In some situations it may be beneficial from a therapeutic and safety point of view to ensure that the primary reservoir can be a standard drug containing vial or cartridge. This would allow the user to deliver a combined therapy when a secondary reservoir is included in the device, but would also allow delivery of the primary compound independently through a standard drug dispense interface in situations, such as, but not limited to, dose splitting (i.e. delivering the complete dose of the primary therapy in two separate injections) or top-up of the primary compound in a way that would prevent the potential risk of double dosing of the secondary compound.

A particular benefit of Applicants' proposed system and method is that the use of two multi-dose reservoirs makes it is possible to tailor dose regimes when required, especially where a titration period is necessary for a particular drug. In an example, a set of drug delivery devices may be provided that have second dose dial components and/or reservoirs that have different properties, and thus result in different fixed doses of a second medicament. The drug delivery devices could be supplied in a number of titration levels with obvious differentiation features such as, but not limited to, aesthetic design of features or graphics, numbering etc, so that a user could be instructed to use the supplied drug delivery devices in a specific order to facilitate titration. Alternatively, the prescribing physician may provide the patient with a number of "level one" titration drug delivery devices and then when these were finished, the physician could then prescribe the next 'level'.

A further feature of an example of Applicants' proposed system and method is that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant, or who have dexterity or computational difficulties. The use of one injection instead of two reduces the possibility for user errors and so may increase patient safety.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

Figure 1:
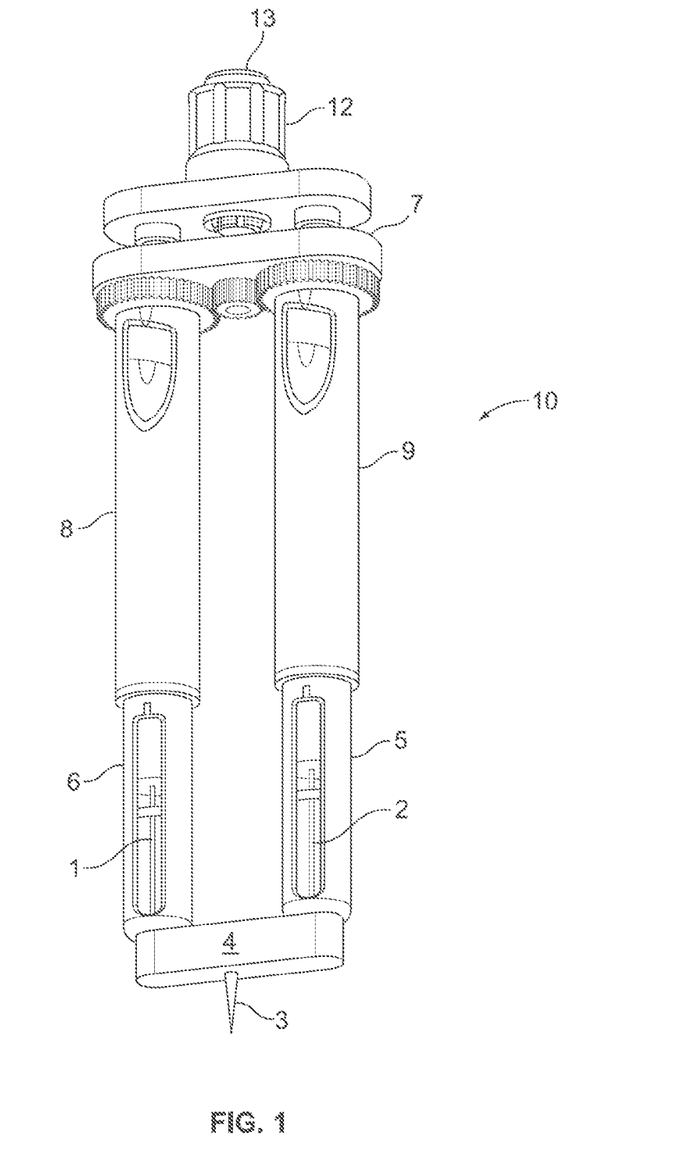
FIG. 1 illustrates a drug delivery system in accordance with an example of Applicants' disclosure, the drug delivery system having two multi-dose reservoirs positioned side-by-side containing a primary medicament and a secondary medicament, respectively.
Figure 2:
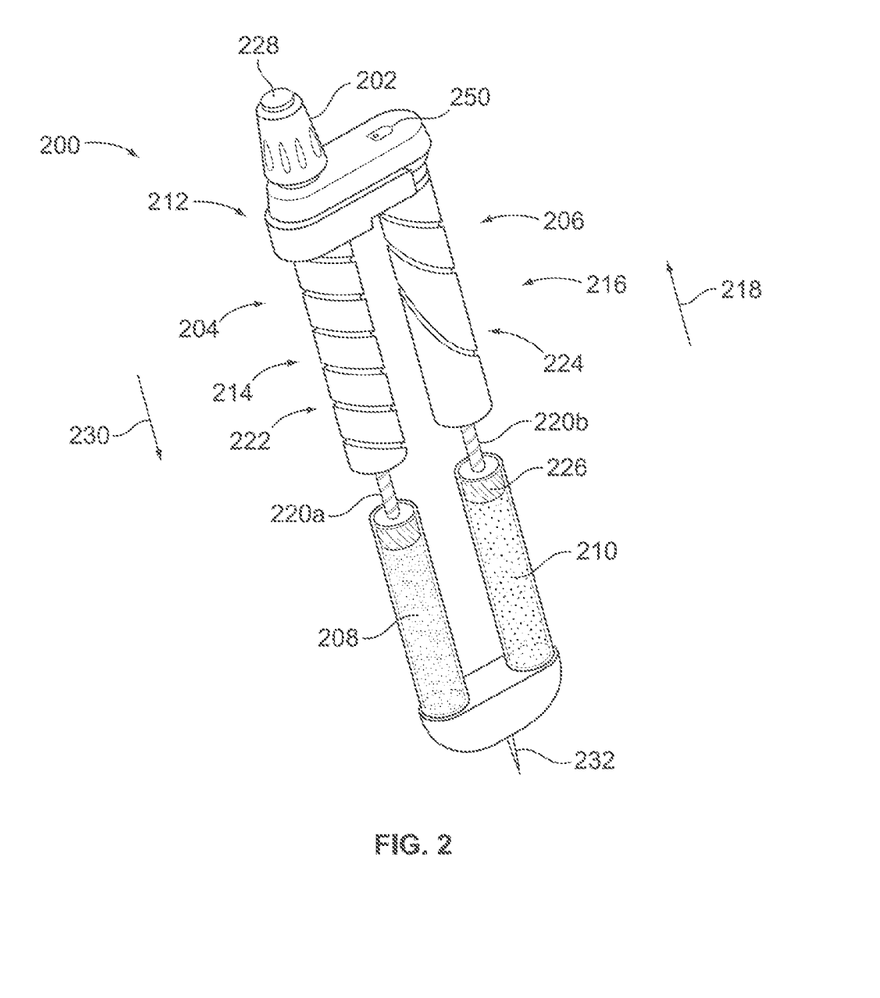
FIG. 2 illustrates another drug delivery system in accordance with an example of Applicants' disclosure.
Figure 4:
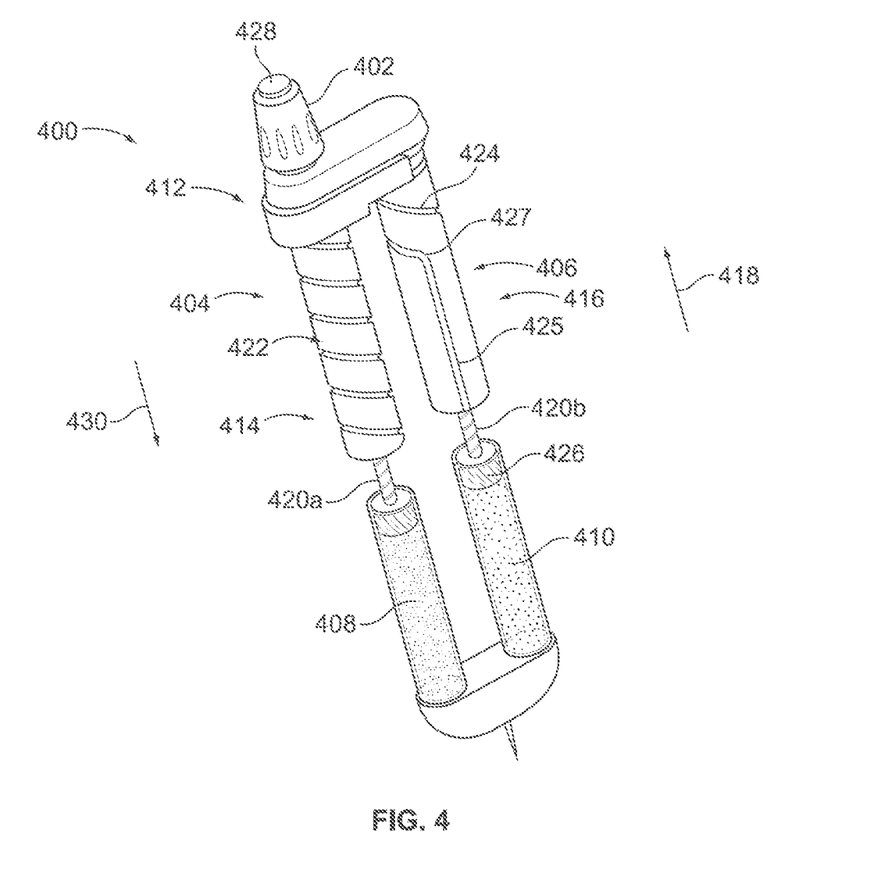
FIG. 4 illustrates another drug delivery system in accordance with an example of Applicants' disclosure.

The drug delivery system of the present disclosure administers a non-user settable or fixed or predetermined dose of a second medicament (secondary drug compound) and a variable dose of a first medicament (primary drug compound) through a single output or drug dispense interface. Setting the dose of the primary medicament by the user automatically determines the fixed dose of the second medicament. In an example the drug dispense interface is a needle cannula (hollow needle). FIGS. 1, 2, and 4 illustrate possible examples of Applicants' drug delivery system.

In particular, FIG. 1 illustrates one possible example of Applicants' drug delivery system, where a multi-use injection device 10 has two reservoirs that are positioned side-by-side with one containing a first medicament 1 and the other a second medicament 2. These reservoirs may contain multiple doses of each medicament. Each reservoir may be self-contained and provided as sealed and sterile cartridges. These cartridges can be of different volumes and replaceable when empty or they can be fixed (non-removable) in the system. They can also have pierceable seals or septa to accept needle cannula.

The cartridges may be housed in cartridge holders 5 and 6 that have attachment means compatible with a removable, disposable hub or housing 4 that contains the single dispense interface. In this example the single dispense interface is shown as output needle 3. The hub can be of any design, provided that it allows for fluid communication between the primary and secondary medicaments and the single dispense interface or needle 3. An example design of hub 4 would include what is referred to in the art as a "2-to-1 needle" configuration. Alternatively, it could be a system that accepts commercially-available 'standard' injection needles, such as those configured for attachment to what is generally known in the art as a 'Type A' thread. Although not shown, hub 4 could be supplied by a manufacturer contained in a protective and sterile capsule or container where the user would peel or rip open a seal or the container itself to gain access to the sterile single dispense interface. In some instances it might be desirable to provide two or more seals for each end of the hub. The seal may allow display of information required by regulatory labeling requirements. When a needle is used to deliver the medicaments it is preferred that the hub is designed to be economical and safe for allowing the user to attach a new hub for each injection. Attachment of hub 4 to the multi-use device 10 creates a fluid connection between output needle 3 and medicaments 1 and 2.

The embodiment in FIG. 1 uses a rotational coupling 7 to mechanically link two dose delivery assemblies 8 and 9 in such a way that rotation of single dose setter 12 allows the user to select a dose of the primary medicament 1 and automatically set a fixed or predetermined non-user settable dose of secondary medicament 2. In the embodiment illustrated, the rotational coupling 7 has been embodied as a gear train in which counter-clockwise rotation of the single dose setter causes clockwise rotation of dose dial components (not shown) within the dose delivery assemblies 8 and 9. Example dose dial components are depicted in FIGS. 2 and 4. The fact that both dial components rotate in the same direction (i.e. clockwise) may be beneficial in that it allows both dose delivery assemblies to be of similar construction in terms of the direction of the helically threaded components and is also likely to be more intuitive for a user to understand. Rotational coupling 7 may be constructed such that it moves vertically at the same rate as both of the dial components. This allows it to set and dispense both drug compounds throughout the full operational range of the device.

As will be understood by those skilled in the art, it is convenient to use lead screws or spindles to push on a piston or bung contained within a cartridge of medicament. As such, it is preferred to use spindles in each dose delivery assembly. By varying the spindle pitches it is possible to vary the dose sizes (and dose ratio) in relation to each other. Specifically, this allows variation of the therapeutic profile to suit a specific therapy or patient requirements by providing devices with different dose ratios. The device shown in FIG. 1 could be operated as follows:

a. Counter-clockwise rotation of the dose setter 12 causes counter-clockwise rotation of the drive gear and clockwise rotation of both driven gears in rotational coupling 7. Clockwise rotation of both driven gears forces both dial components in dose delivery assemblies 8 and 9 to rotate in the same direction and follow a helical path out of the body of the device. This operation allows the user to set a target dose of medicament 1, but not medicament 2, which is automatically set by whatever dose is selected for medicament 1.

b. Initiation of the dosing phase begins with the actuation of dispense or dose button 13 by the user. This causes the dial components to rotate.

c. During the dosing phase, the direction of rotation of the single dose setter as well the internal components of both device mechanisms is reversed. The rotational coupling 7 moves back towards the body of the device as both dial components wind back into the mechanisms following their respective helical paths. This reversal of rotation of both mechanisms coupled with the internal overhauling of the spindles by internal drive sleeves (not shown) causes both medicaments to be dispensed in a simultaneous fashion following the fixed ratio profile defined when the user set the target dose of medicament 1.

In addition to altering the relationship of the fixed ratio of medicaments by varying the threaded arrangement of the dose dial components, varying the spindle pitches of the individual device mechanisms in relation to each other may alter the relationship of the fixed ratio of medicaments. Variation of the spindle pitch changes the advance of the spindle during dispense for a given amount of rotation during setting. Differing amounts of advance between the two mechanisms has the effect of creating different dispense ratios between the mechanisms. Variation of the spindle pitches may have the effect of extending the operational window of delivery device 10 in terms of the range of fixed ratios that can be achieved. This may also assist in keeping the spindle pitch in a range that allows resetting should the device be required to be reusable. This means that multiple pen injectors each having a different therapeutic profile can be manufactured. Specifically, this allows variation of the therapeutic profile to suit a specific titration regime and ultimately individual patient requirements.

The attachment means between hub 4 and cartridge holders 5 and 6 can be any known to those skilled in the art, including threads, snap locks, snap fits, luer locks, bayonet, snap rings, keyed slots, and combinations of such connections. The connection or attachment between the hub and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary reservoir to a non-matching injection device.

The shape of the dispense device 10, including hub 4, may be generally oval and/or cylindrical or any other geometric shape suitable for hand manipulation by a user. Additionally, hub 4 could incorporate a safety shield device that would prevent accidental needle sticks and reduce the anxiety experienced by users who suffer from needle phobia.

As mentioned, an example design of Applicants' drug delivery device would include cartridges to contain the medicaments. Cartridges are typically cylindrical in shape and are usually manufactured in glass, sealed at one end with a rubber bung (piston) and at the other end by a rubber septum using a metal ferrule. The dose delivery assemblies are typically powered by a manual action of the user, however, the injection mechanism may also be powered by other means such as a spring, compressed gas or electrical energy.

FIGS. 2 and 4 depict example dose dial components each connected to a collar. The drug delivery devices illustrated in FIGS. 2 and 4 operate in a similar fashion as drug delivery system 10. For clarity, these Figures depict the dose dial components and drug reservoirs without a housing around them. It should be appreciated, however, that a housing may be included to house or cover these various components and provide the features that interface with the thread forms illustrated on the dial components.

In general, these example drug delivery devices include a dose setter, a first dose dial component, a second dose dial component, and a collar. The first dose dial component is configured to select a first dose of a first medicament, and the first dose dial component is operably connected to the dose setter. The second dose dial component is configured to select a second dose of a second medicament. In addition, the first dose dial component and the second dose dial component are connected to the collar. The collar is configured to be moved in a proximal direction by actuation of the dose setter. Further, when the collar is moved in a proximal direction, the first dose dial component and the second dose dial component are configured to move proximally to set a dose "A" for the first medicament with the first dose dial component and set a dose "B" for the second medicament with the second dose dial component.

In an example, the first dose dial component and the second dose dial component are configured such that a ratio of dose "A" of the first medicament and dose "B" of the second medicament is a non-linear dose profile, wherein the dose profile comprises a non-linear relationship between doses "A" of the first medicament and doses "B" of the second medicament. In another example, the first dose dial component and the second dose dial component are configured such that the ratio of dose "A" of the first medicament and dose "B" of the second medicament renders a linear dose profile. Such a linear dose profile may be a linear dose profile where the dose "A" is different from dose "B". In another example, however, the dose "A" may be equal to dose "B" throughout the linear dose profile.

As will be described in greater detail below, the first dose dial component may comprise a first threaded arrangement configured to rotate the first dose dial component, and the second dose dial component may comprise a second threaded arrangement configured to rotate the second dose dial component. In order to achieve these various dose profiles, the threaded arrangements of the first and second dose dial components may be varied.

A first example of a drug delivery device having dose dial components with different threaded arrangements is shown in FIG. 2. In general, FIG. 2 illustrates a drug delivery system that mechanically links two rotationally driven mechanisms by means of a lifting collar. In this example, the first dose dial component is a constant pitch dose dial component and the second dose dial component is a variable pitch dose dial component. The variable pitch dial component enables a non-linear dosing relationship between the primary and secondary medicament.

In particular, FIG. 2 illustrates a drug delivery system 200. Drug delivery system 200 includes a single dose setter 202, a first dose dial component 204 for a first medicament 208, and a second dose dial component 206 for a second medicament 210. The first and second dose dial components 204, 206 are connected to a collar 212 that acts as a lifting collar. In addition, the first dose dial component 204 is operably connected to the single dose setter 202. The component 204 includes a first threaded arrangement 214. Further, the second dose dial component 206 includes a second threaded arrangement 216. As shown in FIG. 2, the second threaded arrangement 216 is different than the first threaded arrangement 214. The threaded arrangements may take various forms. Example forms in accordance with Applicants' disclosure are shown in FIGS. 2 and 4; however, it should be understood various other examples are possible as well. Further, in some examples, the threaded arrangements of the first dose dial component and the second dose dial component may be the same.

Activation of the dose setter 202 sets a user-settable dose "A" of a first medicament 208 and forces the collar 212 to move in a proximal direction 218. Movement in the proximal direction 218 forces the first dose dial component 204 and the second dose dial component 206 to each move a given proximal distance. The proximal distance corresponds to the dose "A" of the first medicament dialed by the user. In contrast to an arrangement where the threaded arrangements of both dial components are the same, however, the first threaded arrangement and the second threaded arrangement cause the first dose dial component to rotate a different amount than the second dose dial component. This different amount of rotation causes a set dose "A" of the first medicament to be different than a set dose "B" of the second medicament.

In an example, each dial component that the user rotates to set a dose is clutched to a drive component (not shown) during dialing, so that both the dial component and the drive component rotate together. Each drive component may be in threaded engagement with a separate spindle, such as spindles 220a and 220b. Each drive component is arranged such that the respective spindle does not advance when the dose setter 202 is rotated by a user. However, during dispense, the drive component is de-coupled from the dial component and instead coupled to the housing (not shown) such that as the dial returns to its original start position, the drive component moves substantially axially into the housing so as to advance the spindle.

During drug delivery, a user may (i) set the dose, (ii) initiate the dispense of the dose, and then (iii) deliver the dose (i.e., dispense the first and second medicament). Setting of the dose "A" of the first medicament automatically sets a pre-determined dose "B" of the second medicament. The operation of the drug delivery system 200 during these steps is described in detail below.

During the setting of the dose, rotation of the dose setter 202 forces the dose dial component 204 to rotate around a helical path, thus withdrawing it out of the device housing (not shown) in proximal direction 218. This action raises the lifting collar 212 and hence forces dial component 206 to also be lifted vertically in proximal direction 218. The dose dial component 206 also rotates, in a fashion defined by the interaction of the variable helical portion 224 of dial component 206 with the device housing (not shown). As dial component 204 has a constant pitch helical thread 222, dose dial component 204 rotates at a constant rate. However, dial component 206 may rotate at a non-constant rate, thereby giving rise to a non-linear dose profile (e.g., the profile shown in FIG. 3a and described in greater detail below).

This non-linearity arises from the fact that during dose setting, the dose dial component 206 rotates at rate that gets progressively slower. In other words, the pitch of dial component 206 is progressively increasing (and thus the number of rotations for a given amount of axial travel decreases) compared to the rotation rate that occurs when a standard pitch is used (e.g., the standard pitch of dose dial component 204). In the case depicted in FIG. 2, a progressively slower rate of rotation gives rise to a situation where spindle 220b moves away from bung 226. This movement is caused because the internal thread pitch of the dialing mechanism (e.g., the drive sleeve (not shown)) no longer matches the spindle thread pitch. The gap between bung 226 and spindle 220b increases as the amount of drug compound 208 set increases.

Initiation of the dispense phase may begin with the actuation of the dispense component that allows disengagement of the individual device mechanism clutch elements. As described above, the dial components 204, 206 may be coupled to respective drive components during dialing and may decouple during dispense. In the example of FIG. 2, the dose setter 202 includes a dose button 228 that facilitates disengagement of the clutch elements during the dosing phase.

During the dispense phase, the user depresses the dose button 228 and drives the dose setter 202 axially in the distal direction 230. Dial component 204 winds back down following a helical path defined by helical thread 222, and this forces the lifting collar 212 to move in the same axial direction 230. This action causes the first medicament 208 to be dispensed via the single dispense interface or needle 232. Simultaneously, the lifting collar 212 forces dial component 206 to move back axially in direction 230. For the same reasons as described above with reference to the 'setting' phase, dial component 206 may rotate at a non-constant rate during the dosing phase. This effectively means that the non-linear relationship is maintained during the dispensing phase, allowing simultaneous drug delivery of both compounds to occur in a non-linear fashion.

The gap that had been opened up between spindle 220b and bung 226 during the setting phase leads to what may be referred to herein as "lost motion" during the dosing phase. As used herein, lost motion refers to movement of a spindle without dispensing medicament as the gap between the spindle and bung is closed. With respect to this example of FIG. 2, lost motion occurs during movement of spindle 220b without dispensing medicament from the reservoir holding second medicament 210. Provided that the device has been primed correctly prior to the first use (which is a standard practice known in the art for such drug delivery devices), the "lost motion" does not affect the dose accuracy of the dose of second medicament 210 set by the device. The gap introduced during setting is effectively cancelled out by the "lost motion" during the dispense phase.

Beneficially, the differing threaded arrangements 214, 216 of the dose dial components 204, 206 allow the drug delivery system to follow a non-linear dose profile. In the example of FIG. 2, the threaded arrangement 214 comprises a constant pitch helix 222, while the threaded arrangement 216 comprises a variable pitch helix 224. The variable pitch helix 224 creates different rates of rotation of dial component 206 (compared to dial component 204) when it is being lifted by the lifting collar 212. As described above, these differing rates of rotation allow the system 200 to operate in a fixed, non-linear ratio drug delivery mode.

Figure 3A:
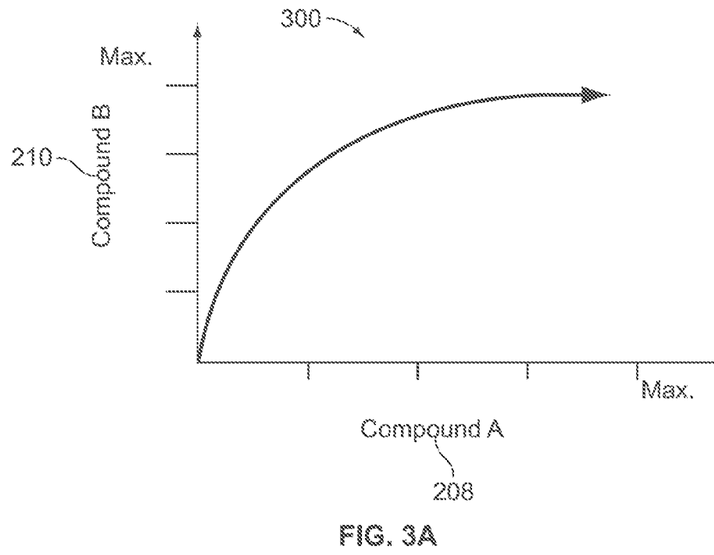
FIG. 3a illustrates an example possible dose profile for the drug delivery system illustrated in FIG. 2.
Figure 3B:
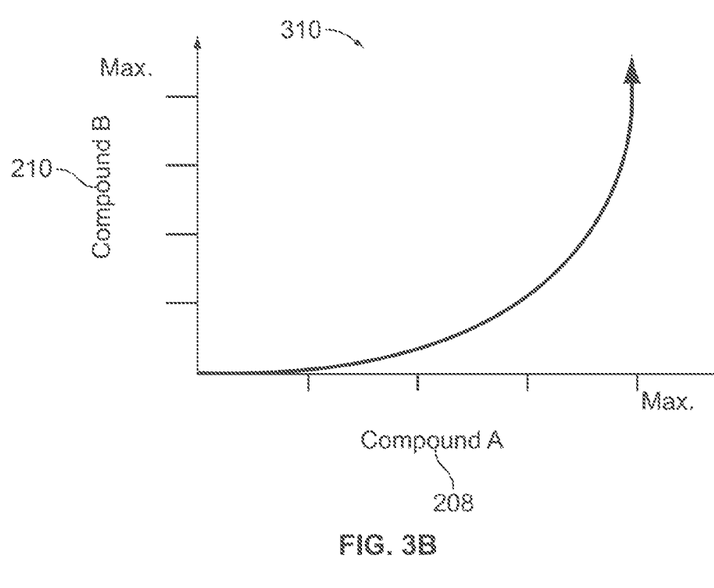
FIG. 3b illustrates another example possible dose profile for a drug delivery system in accordance with an example of Applicants' disclosure.

The rate of change of the helix pitch (in addition to its start point and end point) may be altered to tailor the non-linear ratio to meet a specific, desired therapy profile. Thus, a drug delivery system in accordance with Applicants' disclosure offers a particular target therapeutic profile of a fixed, non-linear ratio (i.e., the relationship between the size of the delivered dose of one medicament and that of the other medicament is fixed, but is non-linear in nature). FIGS. 3a-b depict example fixed, non-linear dose profiles that may be achieved by a drug delivery system in accordance with Applicants' disclosure.

In particular, FIG. 3a depicts a dose profile 300 that may be achieved by the drug delivery device 200. In dose profile 300, the rate of change of the second medicament 210 delivered in relationship to first medicament 208 decreases for larger doses of medicament 208. In other words, the relative increase in the size of dose of the second medicament 210 does not keep pace with the corresponding increase in the size of dose of the first medicament 208, and this effect is due to the variable helix pitch 224 increasing at the distal end of the dose dial component 206.

FIG. 3b depicts another possible dose profile 310 that is achievable with a drug delivery system similar to drug delivery system 200. This dose profile 310 may be achieved by altering the threaded arrangement 216. In particular, the threaded arrangement 216 may be altered to make the large pitch at the proximal end of the dose dial component 206 and the smaller pitch at the distal end of the dose dial component 206. In dose profile 310, the rate of change of the second medicament 210 delivered in relationship to first medicament 208 increases for larger doses of medicament 208.

Figure 3C:
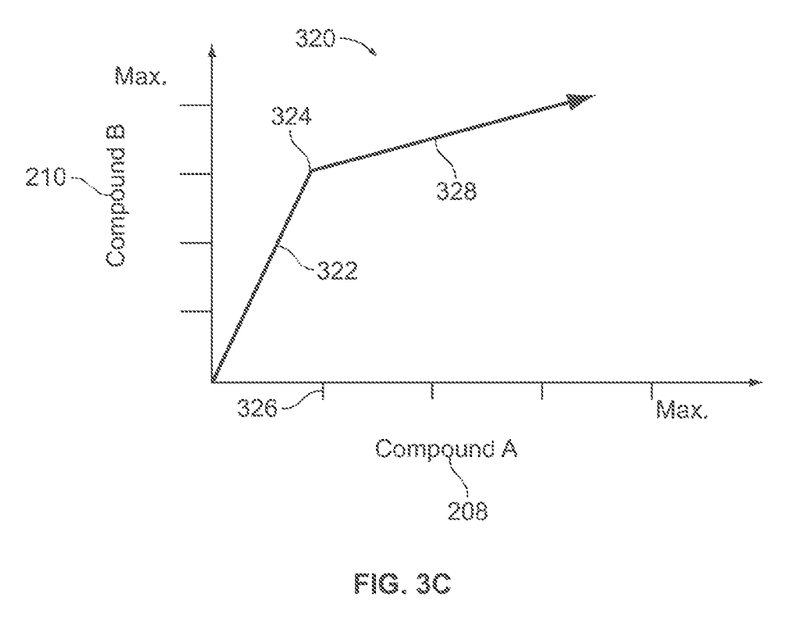
FIG. 3c illustrates another example possible dose profile for a drug delivery system in accordance with an example of Applicants' disclosure.

FIG. 3c illustrates another example possible dose profile for a drug delivery system similar to the system 200. Dose profile 320 begins with a fixed ratio 322 between the first medicament 208 and the second medicament 210. The profile then switches at point 324 (which corresponds to a dose 326 of the first medicament 208) to a second linear relationship 328 between the first medicament 208 and the second medicament 210. This second linear relationship 328 has a different fixed ratio between the first medicament 208 and the second medicament 210, and thus the overall dose profile 320 is non-linear. This profile 320 may be achieved by altering the threaded arrangement 216 to include a step change in the helix. As yet another example possible dose profile for a drug delivery device similar to the device 200, the dose profile could be a linear dose profile.

Another example drug delivery system 400 is shown in FIG. 4. This drug delivery system 400 is similar in many respects to system 200, and thus is not described in as great of detail. It should be explicitly noted, however, that many possibilities and permutations described above with respect to system 200 may equally apply to system 400. The threaded arrangement of the second dose dial component in system 400 is different from the threaded arrangement of the second dose dial component in system 200, thereby leading to a different dose profile than system 200.

In this example, the second drive component is comprised of two distinct, but continuous, sections. In particular, the threaded arrangement 416 includes a helically threaded section 424 and a straight groove section 425. This change from a helical thread 424 to a straight groove 425 effectively limits the delivery of the second medicament 410 to a fixed dose after a given amount of the first medicament 408 is dialed. As shown, dose dial component 404 has threaded arrangement 414 with a constant pitch helical thread 422. Note that there may be a fillet/round on the transition point between helically threaded section 424 and a straight groove section 425.

Figure 5:
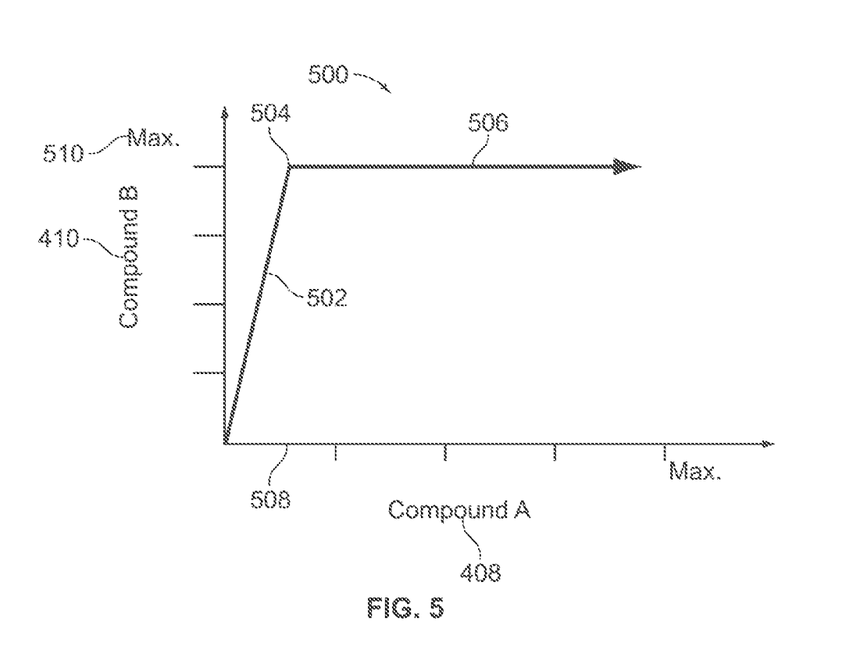
FIG. 5 illustrates an example possible dose profile for the drug delivery system illustrated in FIG. 4.

An example dose profile that may be achieved with the device 400 is shown in FIG. 5. Dose profile 500 begins with a fixed linear ratio 502 between the first medicament 408 and the second medicament 410. The profile then switches at point 504 (which corresponds to a dose 508 of first medicament 408) to a fixed dose portion 506. After reaching the transition point 504, the dial component 404 continues to rotate, whereas dial component 406 ceases to rotate and thus does not set a higher dose of second medicament 410. It should be appreciated that the point at which the dose profile switches from a fixed ratio to a fixed dose (the transition point) can be altered by adjusting the point at which the helically threaded section changes to a straight groove section, and the manner in which this transition is made. Further, the straight groove section could be located at the proximal end of the dose dial component and the helically threaded section could be located at the distal end of the dose dial component.

As discussed above with respect to FIG. 2, during drug delivery, a user may set the dose, initiate the dispense of the medicament, and then deliver/dispense the dose. The operation of the drug delivery system 400 during these steps is described in detail below. During the setting of the dose, rotation of the dose setter 402 forces the dose dial component 404 to rotate around a helical path, therefore translating it out of the device housing (not shown) in proximal direction 418. This action raises the lifting collar 412 and hence forces dial component 406 to also be lifted vertically in proximal direction 418. Initially, the dose dial component 406 also rotates, in a fashion defined by the helical portion 424 of dial component 406.

Initially both dose dial component 404 and dose dial component 406 rotate inwards at a constant rate giving rise to a linear dose setting profile (i.e., a fixed ratio of first medicament 408 to first medicament 410) (see FIG. 5). However, when dial component 404 is wound out past a transition point that corresponds to point 427, dose dial component 406 enters the straight groove section 425. Dose dial component 406 then ceases to rotate but continues to travel axially in proximal direction 418. However, without rotation, dial component 406 is unable to be set to higher doses. Thus, this straight groove section 425 effectively limits the maximum dose of medicament 410 that can be dialed to a fixed value (e.g., maximum dose 510 shown in FIG. 5).

In the straight groove section 425, the dose dial component 406 forces the spindle 420b to rotate in a direction opposite to the direction it rotates during dispense. This action lifts the spindle 420b and a bearing (not shown) away from bung 426, creating a gap between spindle 420b and bung 426. As discussed above with respect to FIG. 2, this gap does not affect the set dose of medicament 410 as the gap is closed without dispensing of medicament 410 during the dispense phase.

Initiation of the dispense phase may begin with the actuation of the dispense component that allows disengagement of the individual device mechanism clutch elements. As described above, the dial components 404, 406 may be coupled to respective drive components during dialing and may decouple during dispense. In the example of FIG. 4, the dose setter 402 includes a dose button 428 that facilitates disengagement of the clutch elements during the dosing phase.

During the dispense phase, the user depresses the dose button 428 and drives the dose setter 402 in the distal direction 430. Dial component 404 winds back down in distal direction 430, following a helical path and forces the lifting collar 412 to move in the same direction. This action (in addition to the drive component moving axially towards the device and overhauling the spindle 420a) causes first medicament 408 to be dispensed. Simultaneously, the lifting collar 412 forces dial component 406 to move back down in distal direction 430. As dose dial component 406 is in the straight groove section 425, the action of the lifting collar 412 will force drive component 406 to slide along the straight portion of the threads. This sliding movement (as opposed to rotation) along the straight grooves does not instigate dosing of second medicament 410. The spindle 420b and bearing (not shown) rotate in the dispensing direction and move downward axially towards bung 426. This effectively reverses the action (i.e., the lifting of the spindle 420b and bearing away from the bung 426) which occurred during the setting phase. Since spindle 420b is not in contact with bung 426, there is no dispensing of second medicament 410 yet. It has been prevented from dosing in relation to higher levels of first medicament 408. Second medicament 410 has thus been limited to a fixed dose as defined by the position of the transition point 427.

Once the lifting collar 412 has moved dose dial component 406 to the transition point 427 where the thread changes from straight to helical, the dose dial component 406 begins to rotate. This rotation of dose dial component 406 (coupled with the continued axial travel of the drive component which overhauls spindle 420b) causes the second medicament 410 to be dispensed simultaneously with first medicament 408. The continued rotation of dial component 404 (coupled with the continued axial travel of the corresponding drive component) means that first medicament 408 continues to be dispensed until the dose dial component 404 reaches its initial (i.e., zero) position when dispensing stops.

Figure 6:
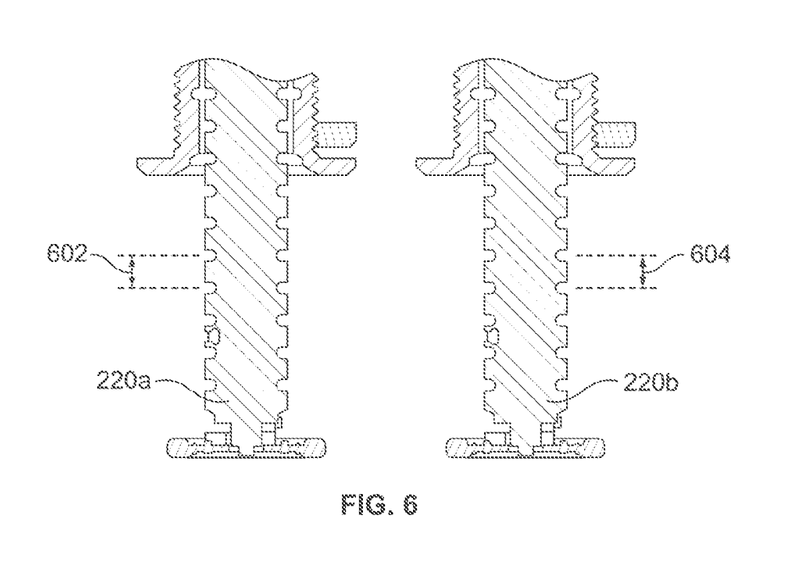
FIG. 6 illustrates example spindles of an example drug delivery system in accordance with an example of Applicants' disclosure.

FIG. 6 illustrates example spindles on an example drug delivery system in accordance with an example of Applicants' disclosure. As mentioned above, in given examples of Applicants' disclosure, the therapeutic profile can be further controlled by varying the pitches between the spindles in the drug delivery devices, such as spindles 220a and 220b. Although the pitch of spindle 220a can be altered compared to the pitch of spindle 220b, the pitch on any one spindle preferably does not vary along its length because a dose is directly related to the rotation of the dial (or drive) component (and hence the spindle relative to the housing) and this should not vary from dose to dose, if the same dose is dialed each time. Further, the dose is directly proportional to the rotation of the dial member during dialing and this rotation is also proportional to the rotation of the spindle during dispense. Therefore, if the pitch 602 of the spindle 220a is reduced, the amount of the first medicament 208 dispensed is reduced by a proportional amount whatever the dose dialed. Varying the pitches 602, 604 of the spindles 220a, 220b of the device may be useful in extending the possible range of non-linear variations that are mechanically feasible within examples of the disclosed device. In addition, spindle-pitch variations may be useful for re-usable platforms that require that the spindles are back wound into the body of the device during cartridge replacement.

As discussed above, in an example of Applicants' disclosure, the drug delivery system may include both a dose dial component and a drive component. In an alternative embodiment, the dose dial component that the user rotates to set a dose could also be the drive component that interfaces with the spindle. In such a case, the spindle may be coupled to the drive component via a one-way coupling. The one-way coupling may allow relative axial movement between the two parts so that, as the drive member is dialed, it rotates by an amount R relative to the housing and spindle. During dispense, the one-way coupling may drive the spindle through the housing by the rotation amount "R" generated during dialing. This one-way coupling could be direct between both parts consisting of, for instance, flexible ratchet arms on the drive component engaging with one-way ratchet pockets, grooves or splines running axially along the length of the spindle.

Alternatively, the coupling may consist of an intermediate drive component that is splined to the spindle allowing axial but not rotational movement between the two components. This intermediate drive component may also be in clutched engagement with the dial component so that, during dialing, this clutch slips allowing the dial to rotate relative to the drive component. However, during dispense it may lock, transferring the rotation of the dose dial component (as it spins back into the housing) into rotation of the drive member and hence the spindle. An example advantage of this approach of using an intermediate drive member is that it is possible to design the clutch so that it will slip in both dialing up and dialing down enabling the user to correct a dialed dose.

In either of the case where the dose dial component and drive sleeve are separate elements or where they are the same element, the dose dispensed is preferably proportional to the rotation "R" of the dial member relative to the housing when the dose is dialed, and is not proportional to the axial displacement of the dial member relative to the housing. Hence when the axial displacement of two dial members are linked as described above, the dose dispensed from each will be in proportion to the individual rotation of each dial member. This rotation is related to the pitch of each individual dial member and the axial displacement. For instance, dose dial component 204 could have a constant pitch and dose dial component 206 could have a variable pitch.

Alternatively, in another example, dose dial component 204 could have a decreasing pitch as the device is dialed and dose dial component 206 could have an increasing pitch. In this alternative embodiment, however, the total volume of drug dispensed per amount of axial travel of the two linked dial members could be designed to remain constant ensuring a constant dispense force profile during the delivery of the compound dose, the majority of second medicament being delivered at the end of the dose and the majority of the first medicament being delivered at the start of the dose.

In some situations, it may be beneficial for a user to prime the drug delivery device before setting and delivering the full dose of medicament. In an example, a drug delivery device in accordance with Applicants' proposed concept may include a priming arrangement, e.g. a priming button, such as priming button 250 shown in FIG. 2, to facilitate priming of the device. This priming arrangement may be configured to disengage the second dose dial component from the collar, preventing the second dose dial component to move proximally when the collar is moved in a proximal direction. A user may then prime the device using only the first medicament, because movement of the collar in the proximal direction will only move the first dose dial component in the proximal direction. Thus, the user may set and dispense a priming dose (e.g., a dose of 2 units) of the first medicament. After the user primes the device, the collar and second dose dial component may reengage, and the user may then set the drug delivery device. The addition of such a priming arrangement that allows for priming with only the first medicament may be beneficial in a scenario where the second medicament does not require repeated priming or if the second medicament is a particularly expensive medicament (relative to the expense of the first medicament).

In addition, although shown as a "2-to-1" needle, the injection component could be embodied as two separate needles. A separate needle would be provided for each separate medicament. In addition, the disclosed drug delivery system could be embodied in such a way as to allow for the injection of drug compounds from more than two primary packs. This would involve the addition of additional drive mechanisms and an extension of the lifting collar.

The disclosed drug delivery system may be suited towards a modular disposable or re-usable platform in terms of managing drug wastage. This is because there is a risk of one medicament being finished before the other unless there is a strict 1:1 ratio between the two medicaments. However, where each side is resettable, new primary packs can be inserted and the device can continue to be used. Possible embodiments for a modular disposable platform could, but are not limited to, involve the replacement of the entire device mechanism fitted with a new primary pack. Suitable re-engagement features may be integrated into the device platform to facilitate the alignment and fastening of the individual device mechanisms together in a robust and user friendly fashion. It is possible that such features could be arranged to define the permissible functionality of the two individual elements on their own.

A possible re-usable platform would feature spindles that could be back wound into their respective devices once they had reached the limits of travel. In addition to this functionality, the platform would feature a means of replacing both primary packs after the resetting of one or both spindles.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A drug delivery device comprising:
a single dose setter;
a primary reservoir configured to contain a first medicament;
a secondary reservoir configured to contain a second medicament;
a first dose dial component configured to select a first dose of the first medicament, wherein the first dose dial component is operably connected to the single dose setter,
a second dose dial component configured to select a second dose of the second medicament,
a collar, wherein the first dose dial component and the second dose dial component are connected to the collar;
wherein the collar moves in a proximal direction by actuation of the single dose setter, and when the collar moves in a proximal direction, the first dose dial component and the second dose dial component move proximally to set a variable dose "A" for the first medicament with the first dose dial component and to automatically set a non-user settable, predetermined dose "B" for the second medicament with the second dose dial component,
wherein the first dose dial component and the second dose dial component are configured such that a ratio of dose "A" of the first medicament and dose "B" of the second medicament is a nonlinear dose profile, wherein the dose profile comprises a non-linear relationship between doses "A" of the first medicament and doses "B" of the second medicament.

2. A drug delivery device according to claim 1, wherein the first dose dial component and the second dose dial component are configured such that the ratio of dose "A" of the first medicament and dose "B" of the second medicament renders a linear dose profile.

3. A drug delivery device according to claim 2, wherein the dose "A" is different from dose "B".

4. A drug delivery device according to claim 2, wherein the dose "A" is equal to dose "B".

5. A drug delivery device according to claim 1, where the dose profile comprises at least a first part and a second part, wherein the first part has a first linear ratio and the second part has a second linear ratio different from the first linear ratio.

6. A drug delivery device according to claim 1, where the dose profile comprises at least two parts, wherein, in one part of the at least two parts, the dose "A" of the first medicament is variable and the dose "B" of the second medicament is fixed.

7. A drug delivery device according to claim 1, wherein the first dose dial component comprises a first threaded arrangement configured to rotate the first dose dial component; and wherein the second dose dial component comprises a second threaded arrangement configured to rotate the second dose dial component.

8. A drug delivery device according to claim 7, wherein the second threaded arrangement is different than the first threaded arrangement.

9. A drug delivery device according to claim 7, wherein the first threaded arrangement comprises a helical thread of a constant pitch, wherein the second threaded arrangement comprises a first portion and a second portion, and wherein the first portion is a helical thread and the second portion is a straight thread.

10. A drug delivery device of claim 7, wherein the first threaded arrangement comprises a helical thread of a constant pitch, and wherein the second threaded arrangement comprises a helical thread of a different constant pitch.

11. A drug delivery device of claim 7, wherein the first threaded arrangement is a helical thread of a constant pitch, and wherein the second threaded arrangement is a helical thread of a variable pitch.

12. A drug delivery device according to claim 1, comprising a single dispense interface configured for fluid communication with the primary reservoir and with the secondary reservoir of medicament containing, further configured to allow said dose "A" and said dose "B" to be delivered from the device.

13. A drug delivery device according to claim 12, wherein the single dispense interface comprises a hollow needle cannula.

14. A drug delivery device according to claim 1, comprising a priming arrangement configured to disengage the second dose dial component from the collar preventing the second dose dial component to move proximally when the collar is moved in a proximal direction.

* * * * *